US010254297B2

(12) United States Patent
McConnell et al.

(10) Patent No.: US 10,254,297 B2
(45) Date of Patent: Apr. 9, 2019

(54) ASSAY FOR METHOXETAMINE (71) Applicant: Randox Laboratories Ltd, Crumlin (GB)

(72) Inventors: Ivan McConnell, Crumlin (GB); Philip Lowry, Crumlin (GB); Elouard Benchikh, Crumlin (GB); Peter Fitzgerald, Crumlin (GB)

(73) Assignee: Randox Laboratories Ltd. (GB)

( * ) Notice: Subject to any disclaimer, the term of this patent is extended or adjusted under 35 U.S.C. 154(b) by 161 days.

(21) Appl. No.: 15/200,558

(22) Filed: Jul. 1, 2016

(65) Prior Publication Data
US 2017/0003308 A1 Jan. 5, 2017

(30) Foreign Application Priority Data

Jul. 3, 2015 (GB) .................................. 1511725.2

(51) Int. Cl.
*G01N 33/94* (2006.01)
*C07K 14/435* (2006.01)
*C07K 16/44* (2006.01)
*C07C 225/20* (2006.01)
*C07C 229/14* (2006.01)

(52) U.S. Cl.
CPC ........... *G01N 33/94* (2013.01); *C07C 225/20* (2013.01); *C07C 229/14* (2013.01); *C07K 14/43504* (2013.01); *C07K 16/44* (2013.01); *C07K 2317/33* (2013.01); *C07K 2317/92* (2013.01)

(58) Field of Classification Search
CPC ................ C07C 225/20; C07C 229/14; C07K 14/43504; C07K 16/44; C07K 2317/33; C07K 2317/92; G01N 33/94
See application file for complete search history.

(56) References Cited

U.S. PATENT DOCUMENTS

| 2003/0224447 | A1 | 12/2003 | McConnell et al. |
| 2014/0357642 | A1* | 12/2014 | Chatlton ............ A61K 31/4985 |
| | | | 514/250 |

FOREIGN PATENT DOCUMENTS

| EP | 1988398 | 11/2008 |
| EP | 2887070 | 6/2015 |

OTHER PUBLICATIONS

Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Szurdoki et al., "Important Factors in Hapten Design and Enzyme-Linked Immunosorbent Assay Development," in Immunoanalysis of Agrochemicals; Nelson, J., et al.; ACS Symposium Series, 1995, vol. 586, Chapter 4, pp. 39-63.*
Englebienne, "Immune and Receptor Assays in Theory and Practice," CRC Press, 2000, p. 308.*
Alpha Diagnostic International, Product Data Sheet, Cat# 700-101, "Keyhole limpet hemocyanin (KLH, hemocyanin) coated ELISA plates," posted on Internet Apr. 10, 2013.*
Zawilski, J.B., et al., Methoxetamine—A novel recreational drug with potent hallucinogenic properties, Toxicology Letters, Aug. 2014, vol. 230, No. 3, pp. 402-407.
Kjellgren, A., et al., Methoxetamine (MXE)—A Phenomenological Study of Experiences Induced by a "Legal High" from the Internet, Journal of Psychoactive Drugs, Aug. 2, 2013, vol. 45, No. 3, pp. 276-286.
World Health Organization, Expert Committee on Drug Dependence, Methoxetamine, Critical Review Report, Expert Committee on Drug Dependence, 36th Meeting, Geneva, Jun. 16-20, 2014, 22 pages.
Hays, P.A., et al., The Characterization of 2-(3-Methoxyphenyl)-2-(ethylamino)cyclohexanone (Methoxatamine), Microgram Journal, 2013, vol. 9, No. 1, pp. 3-17.
Menzies, et al., Characterizing metabolites and potential metabolic pathways for the novel psychoactive substance methoxetamine, Drug Testing and Analysis, vol. 6, No. 6, pp. 506-515 Nov. 5, 2013.

* cited by examiner

*Primary Examiner* — Galina Yakovleva
(74) *Attorney, Agent, or Firm* — Gavrilovich, Dodd & Lindsey LLP (57) ABSTRACT

Components for enabling immunodetection of methoxetamine are described including immunogens, haptens, antibodies and kits.

9 Claims, 7 Drawing Sheets

Methoxetamine

Ketamine

Norketamine

Phencyclidine

Tramadol

Tilidine

N-Desethylmethoxetamine

Figure 4

| Conc. | Methoxetamine | | | Ketamine | | | Norketamine | | | PCP | | | Tramadol hydrochloride | | |
|---|---|---|---|---|---|---|---|---|---|---|---|---|---|---|---|
| ng/ml | Ave OD | %CV | B/Bo | Ave OD | %CV | B/Bo | Ave OD | %CV | B/Bo | Ave OD | %CV | B/Bo | Ave OD | %CV | B/Bo |
| 0 | 1.843 | 2 | 100 | 1.844 | 0.8 | 100 | 1.867 | 0.7 | 100 | 1.862 | 0.8 | 100 | 1.881 | 2.1 | 100 |
| 0.15625 | 1.413 | 1.4 | 77 | 1.862 | 0.1 | 101 | 1.854 | 0.9 | 99 | 1.801 | 1.1 | 97 | 1.829 | 1.5 | 97 |
| 0.3125 | 1.133 | 3.3 | 61 | 1.842 | 0.5 | 100 | 1.833 | 0.1 | 98 | 1.758 | 0.9 | 94 | 1.793 | 1.1 | 95 |
| 0.625 | 0.770 | 3.1 | 42 | 1.837 | 0.6 | 100 | 1.847 | 1 | 99 | 1.748 | 0 | 94 | 1.838 | 2.4 | 98 |
| 1.25 | 0.515 | 0.1 | 28 | 1.814 | 0.8 | 98 | 1.831 | 0.7 | 98 | 1.722 | 1.6 | 93 | 1.831 | 0 | 97 |
| 2.5 | 0.304 | 1.9 | 16 | 1.787 | 0.4 | 97 | 1.826 | 0.5 | 98 | 1.660 | 1.4 | 89 | 1.814 | 0.3 | 96 |
| 5 | 0.180 | 1.2 | 10 | 1.730 | 1.8 | 94 | 1.784 | 0.7 | 96 | 1.562 | 2 | 84 | 1.770 | 0.4 | 94 |
| 10 | 0.108 | 3.9 | 6 | 1.686 | 0.5 | 91 | 1.722 | 1.3 | 92 | 1.473 | 0.4 | 79 | 1.721 | 0.4 | 92 |
| IC$_{50}$ | 0.47ng/ml | | | >10ng/ml | | | >10ng/ml | | | >10ng/ml | | | >10ng/ml | | |
| %CCR | 100 | | | <4.7 | | | <4.7 | | | <4.7 | | | <4.7 | | |

| Conc. | O-Desmethyl-cis-Tramadol | | | Tilidine hydrochloride | | | 2-(3-Methoxyphenyl) cyclohexanone | | | N-Desethyl Methoxetamine AB-10-182F2 | | | N-Desmethyl Tramadol | | |
|---|---|---|---|---|---|---|---|---|---|---|---|---|---|---|---|
| ng/ml | Ave OD | %CV | B/Bo | Ave OD | %CV | B/Bo | Ave OD | %CV | B/Bo | Ave OD | %CV | B/Bo | Ave OD | %CV | B/Bo |
| 0 | 1.911 | 1.9 | 100 | 1.864 | 0.5 | 100 | 1.833 | 1.1 | 100 | 1.789 | 0.4 | 100 | 1.890 | 0.1 | 100 |
| 0.15625 | 1.921 | 1.3 | 100 | 1.838 | 0.1 | 99 | 1.843 | 2.6 | 101 | 1.570 | 0.3 | 88 | 1.878 | 0.9 | 99 |
| 0.3125 | 1.931 | 1.6 | 101 | 1.838 | 0.3 | 99 | 1.818 | 3.6 | 99 | 1.414 | 0.4 | 79 | 1.847 | 0.2 | 98 |
| 0.625 | 1.934 | 1 | 101 | 1.895 | 1.1 | 102 | 1.862 | 2.2 | 102 | 1.267 | 0.9 | 71 | 1.861 | 0.4 | 98 |
| 1.25 | 1.924 | 2.9 | 101 | 1.886 | 0.1 | 101 | 1.849 | 0.8 | 101 | 1.034 | 5.5 | 58 | 1.862 | 0.8 | 98 |
| 2.5 | 1.945 | 2.4 | 102 | 1.870 | 1.5 | 100 | 1.865 | 1.3 | 102 | 0.819 | 1.9 | 46 | 1.839 | 0 | 97 |
| 5 | 1.917 | 0.9 | 100 | 1.878 | 0.4 | 101 | 1.847 | 1.8 | 101 | 0.583 | 0.1 | 33 | 1.857 | 2.3 | 98 |
| 10 | 1.901 | 0.1 | 99 | 1.869 | 0.3 | 100 | 1.819 | 1.6 | 99 | 0.384 | 4.1 | 21 | 1.787 | 1.8 | 95 |
| IC$_{50}$ | >10ng/ml | | | >10ng/ml | | | >10ng/ml | | | 1.96ng/ml | | | >10ng/ml | | |
| %CCR | <4.7 | | | <4.7 | | | <4.7 | | | 24 | | | <4.7 | | |

Figure 5

| Conc. | Methoxetamine | | | Ketamine | | | Norketamine | | | PCP | | | Tramadol hydrochloride | | |
|---|---|---|---|---|---|---|---|---|---|---|---|---|---|---|---|
| ng/ml | Ave OD | %CV | B/Bo | Ave OD | %CV | B/Bo | Ave OD | %CV | B/Bo | Ave OD | %CV | B/Bo | Ave OD | %CV | B/Bo |
| 0 | 2.294 | 2.9 | 100 | 2.301 | 0.1 | 100 | 2.304 | 0.6 | 100 | 2.297 | 1.7 | 100 | 2.288 | 0.2 | 100 |
| 0.15625 | 1.618 | 2.6 | 71 | 2.263 | 1.1 | 98 | 2.295 | 0.6 | 100 | 2.263 | 0.7 | 99 | 2.286 | 0.1 | 100 |
| 0.3125 | 1.306 | 4.5 | 57 | 2.239 | 0.6 | 97 | 2.283 | 0.3 | 99 | 2.229 | 0.3 | 97 | 2.224 | 0.3 | 97 |
| 0.625 | 0.856 | 1.4 | 37 | 2.145 | 1 | 93 | 2.223 | 0.5 | 96 | 2.186 | 0.4 | 95 | 2.183 | 0.2 | 95 |
| 1.25 | 0.613 | 0 | 27 | 2.195 | 0.1 | 95 | 2.267 | 1.2 | 98 | 2.178 | 0.7 | 95 | 2.267 | 0.2 | 99 |
| 2.5 | 0.404 | 2.3 | 18 | 2.135 | 1.2 | 93 | 2.239 | 0.1 | 97 | 2.112 | 0.7 | 92 | 2.221 | 0.6 | 97 |
| 5 | 0.255 | 2.2 | 11 | 2.048 | 0.1 | 89 | 2.157 | 0.8 | 94 | 1.975 | 0.3 | 86 | 2.150 | 1.2 | 94 |
| 10 | 0.176 | 1.2 | 8 | 1.968 | 0.9 | 86 | 2.128 | 0.5 | 92 | 1.854 | 0.1 | 81 | 2.115 | 0.7 | 92 |
| IC$_{50}$ | 0.39ng/ml | | | >10ng/ml | | | >10ng/ml | | | >10ng/ml | | | >10ng/ml | | |
| %CCR | 100 | | | <3.9 | | | <3.9 | | | <3.9 | | | <3.9 | | |

| Conc. | O-Desmethyl-cis-Tramadol | | | Tilidine hydrochloride | | | 2-(3-Methoxyphenyl) cyclohexanone | | | N-Desethyl Methoxetamine | | | N-Desmethyl Tramadol | | |
|---|---|---|---|---|---|---|---|---|---|---|---|---|---|---|---|
| ng/ml | Ave OD | %CV | B/Bo | Ave OD | %CV | B/Bo | Ave OD | %CV | B/Bo | Ave OD | %CV | B/Bo | Ave OD | %CV | B/Bo |
| 0 | 2.208 | 0.5 | 100 | 2.192 | 0.9 | 100 | 2.201 | 0.8 | 100 | 2.119 | 0.1 | 100 | 2.280 | 0.2 | 100 |
| 0.15625 | 2.186 | 0.3 | 99 | 2.186 | 0.6 | 100 | 2.178 | 1.1 | 99 | 1.842 | 1.4 | 87 | 2.292 | 0.8 | 101 |
| 0.3125 | 2.225 | 0.8 | 101 | 2.183 | 0.3 | 100 | 2.160 | 1.6 | 98 | 1.656 | 2.2 | 78 | 2.251 | 0.6 | 99 |
| 0.625 | 2.199 | 1 | 100 | 2.191 | 0.2 | 100 | 2.179 | 1.6 | 99 | 1.471 | 1.1 | 69 | 2.183 | 1.7 | 96 |
| 1.25 | 2.173 | 1.1 | 98 | 2.150 | 0.6 | 98 | 2.178 | 1.5 | 99 | 1.201 | 0.8 | 57 | 2.241 | 0.9 | 98 |
| 2.5 | 2.148 | 0 | 97 | 2.137 | 1 | 97 | 2.131 | 0.6 | 97 | 0.969 | 0.4 | 46 | 2.184 | 0.9 | 96 |
| 5 | 2.118 | 0.6 | 96 | 2.106 | 0.1 | 96 | 2.105 | 0.9 | 96 | 0.681 | 0.9 | 32 | 2.104 | 0.8 | 92 |
| 10 | 2.120 | 0.1 | 96 | 2.102 | 0.6 | 96 | 2.082 | 0.1 | 95 | 0.467 | 1.2 | 22 | 2.038 | 0.4 | 89 |
| IC$_{50}$ | >10ng/ml | | | >10ng/ml | | | >10ng/ml | | | 1.88ng/ml | | | >10ng/ml | | |
| %CCR | <3.9 | | | <3.9 | | | <3.9 | | | 20.7 | | | <3.9 | | |

| Conc. | Methoxetamine | | | Ketamine | | | Norketamine | | | PCP | | | Tramadol hydrochloride | | |
|---|---|---|---|---|---|---|---|---|---|---|---|---|---|---|---|
| ng/ml | Ave OD | %CV | B/Bo | Ave OD | %CV | B/Bo | Ave OD | %CV | B/Bo | Ave OD | %CV | B/Bo | Ave OD | %CV | B/Bo |
| 0 | 1.907 | 2.6 | 100 | 1.876 | 0.5 | 100 | 1.927 | 0.7 | 100 | 1.909 | 0.4 | 100 | 1.906 | 1 | 100 |
| 0.15625 | 1.490 | 1.7 | 78 | 1.888 | 1.4 | 101 | 1.908 | 1.3 | 99 | 1.884 | 0.3 | 99 | 1.895 | 0.6 | 99 |
| 0.3125 | 1.192 | 2.4 | 62 | 1.858 | 1 | 99 | 1.869 | 1.1 | 97 | 1.882 | 0.9 | 99 | 1.888 | 0.4 | 99 |
| 0.625 | 0.820 | 4.1 | 43 | 1.825 | 1.4 | 97 | 1.852 | 0.6 | 96 | 1.857 | 0.4 | 97 | 1.890 | 0.2 | 99 |
| 1.25 | 0.537 | 4.7 | 28 | 1.818 | 0.4 | 97 | 1.872 | 0.3 | 97 | 1.821 | 0.7 | 95 | 1.875 | 0.8 | 98 |
| 2.5 | 0.320 | 3.1 | 17 | 1.791 | 1.6 | 95 | 1.844 | 0.4 | 96 | 1.759 | 0.6 | 92 | 1.860 | 0.2 | 98 |
| 5 | 0.182 | 0.4 | 10 | 1.718 | 1.5 | 92 | 1.833 | 1.6 | 95 | 1.679 | 0.3 | 88 | 1.810 | 1.8 | 95 |
| 10 | 0.113 | 0.6 | 6 | 1.664 | 0.5 | 89 | 1.777 | 0.5 | 92 | 1.584 | 1.4 | 83 | 1.760 | 1.9 | 92 |
| IC50 | 0.49ng/ml | | | >10ng/ml | | | >10ng/ml | | | >10ng/ml | | | >10ng/ml | | |
| %CCR | 100 | | | <4.9 | | | <4.9 | | | <4.9 | | | <4.9 | | |

| Conc. | O-Desmethyl-cis-Tramadol | | | Tilidine hydrochloride | | | 2-(3-Methoxyphenyl)cyclohexanone | | | N-Desethyl Methoxetamine | | | N-Desmethyl Tramadol | | |
|---|---|---|---|---|---|---|---|---|---|---|---|---|---|---|---|
| | | | | | | | | | | AB-10-182F2 | | | | | |
| ng/ml | Ave OD | %CV | B/Bo | Ave OD | %CV | B/Bo | Ave OD | %CV | B/Bo | Ave OD | %CV | B/Bo | Ave OD | %CV | B/Bo |
| 0 | 1.848 | 0.6 | 100 | 1.856 | 0.4 | 100 | 1.852 | 0.2 | 100 | 1.822 | 0.7 | 100 | 1.922 | 0.7 | 100 |
| 0.15625 | 1.819 | 1.4 | 98 | 1.833 | 0.2 | 99 | 1.818 | 0.2 | 98 | 1.594 | 0.5 | 87 | 1.910 | 0.8 | 99 |
| 0.3125 | 1.845 | 1 | 100 | 1.833 | 0.1 | 99 | 1.808 | 1.1 | 98 | 1.434 | 0.1 | 79 | 1.923 | 0.7 | 100 |
| 0.625 | 1.820 | 0.7 | 98 | 1.853 | 0.5 | 100 | 1.831 | 0.8 | 99 | 1.263 | 0.3 | 69 | 1.902 | 0.3 | 99 |
| 1.25 | 1.838 | 0.6 | 99 | 1.842 | 1.2 | 99 | 1.809 | 1.1 | 98 | 1.053 | 1.3 | 58 | 1.892 | 0.4 | 98 |
| 2.5 | 1.831 | 0.3 | 99 | 1.814 | 0.2 | 98 | 1.779 | 1.4 | 96 | 0.804 | 2.5 | 44 | 1.889 | 0.7 | 98 |
| 5 | 1.816 | 0.5 | 98 | 1.775 | 0.1 | 96 | 1.750 | 0.6 | 94 | 0.580 | 1.7 | 32 | 1.839 | 0.4 | 96 |
| 10 | 1.740 | 0.4 | 94 | 1.741 | 0.3 | 94 | 1.701 | 1.1 | 92 | 0.377 | 3.2 | 21 | 1.757 | 1.5 | 91 |
| IC50 | >10ng/ml | | | >10ng/ml | | | >10ng/ml | | | 1.86ng/ml | | | >10ng/ml | | |
| %CCR | <4.9 | | | <4.9 | | | <4.9 | | | 26.3 | | | <4.9 | | |

Figure 7

ASSAY FOR METHOXETAMINE

RELATED APPLICATIONS

The instant application claims the benefit of priority under 35 USC § 119 to United Kingdom Application No. 1511725.2, entitled "Assay" filed 3 Jul. 2015, the entire contents of which are incorporated herein by reference in their entirety.

BACKGROUND

Methoxetamine, systematic name 2-(3-methoxyphenyl)-2-(ethylamino)cyclohexanone, is an arylcyclohexylamine whose structure is purported to have been based upon ketamine in an attempt to mimic ketamine's dissociative properties. Its main metabolite is 2-amino-2-(3-methoxyphenyl)cyclohexanone also known as N-desethylmethoxetamine; other metabolites include the demethylated parent O-desmethylmethoxetamine and arylhydroxylated derivatives (Zawilska 2014). Its legal status in numerous countries coupled with the facilitating effect of the Internet in relation to accessibility and distribution, has led to its increasing recreational use (Kjellgren and Jonnson 2013; ECCD 2014). The problem of increasing methoxetamine use is being recognised and it is currently banned in several countries including the UK, Japan and Russia. Analysis of samples for its presence is increasing to assess its prevalence as a recreational drug and more disturbingly in post-mortem toxicological screens. To date gas chromatography (GC) and liquid chromatography (LC) linked to mass spectrometry (MS) have been the predominant analytical detection techniques used (ECDD 2014). These techniques require specialist staff for their operation, are expensive and are not amenable to use outside of the laboratory. Furthermore, the mass spectra of methoxetamine and ketamine are similar (Hays et al., 2013) complicating analysis.

REFERENCES

Zawilska J. B. (2014). Toxicology Letters, 230(3): 402-407.
Kjellgren A. and Jonnson K. (2013). Journal of Psychoactive Drugs, 45(3): 276-286. ECDD (2014). Methoxetamine, Critical Review Report, Expert Committee on Drug Dependence, 36th Meeting, Geneva.
Hays P. A., Casale J. F. and Berrier A. L. (2013). Microgram Journal, 9(1): 3-17.

SUMMARY OF THE INVENTION

Described is the first known antibody which specifically binds methoxetamine. The properties of the antibody enable an immunoassay method for the detection and quantification of methoxetamine and its major metabolite N-desethylmethoxetamine. The invention further describes novel haptens and immunogens as well as substrates comprising the antibody.

In one embodiment, the present invention is n immunogen of structure III Structure III wherein: X is —NH— or —N(R)—; R is substituted or unsubstituted alkyl; n is 0 or 1; and accm is an antigenicity conferring carrier material.

In another embodiment, the present invention is an antibody raisable against the immunogen of structure III Structure III wherein: X is —NH— or —N(R)—; R is substituted or unsubstituted alkyl; n is 0 or 1; and accm is an antigenicity conferring carrier material. In one embodiment, the antibody of has <5% competitive cross-reactivity to any one of ketamine, norketamine, tramadol and tilidine compared with a 100% competitive cross-reactivity to methoxetamine. In one embodiment the antibody has an $IC_{50}$ of <10 ng/ml for methoxetamine.

In one embodiment, the present invention is an antibody which binds Structure I'

Structure I' wherein each R' is independently —H or substituted or unsubstituted alkyl; and each substitutable carbon on the cyclohexyl or phenyl rings may be optionally substituted.

In one embodiment, Structure I' is Structure II'

Structure II'

In one embodiment, the antibody of the present invention has <5% competitive cross-reactivity to any one of ketamine, norketamine, tramadol and tilidine compared with a 100% competitive cross-reactivity to methoxetamine.

In one embodiment, the present invention is a method of detecting or determining methoxetamine in a sample comprising: i) contacting the sample with a detecting agent and an antibody of Claim 4; and ii) detecting or determining the amount of detecting agent bound to the antibody.

In one embodiment, the present invention is a kit comprising an antibody of the present invention and optionally a detecting agent.

The antibodies of the present invention are advantageous in that they have a high affinity for both methoxetamine and it's metabolite, and do not have a significant binding affinity for the close structurally related compounds: ketamine and norketamine. In addition, the fact that the antibodies of the present invention have binding affinity for metabolites of methoxetamine increases the accuracy of immunoassays using these antibodies in, for example, urine analysis for law enforcement and employment drug testing.

BRIEF DESCRIPTION OF THE FIGURES

FIG. 5, Antibody binding characteristics to various cross-reactants for antibody derived from sheep 1.
FIG. 6, Antibody binding characteristics to various cross-reactants for antibody derived from sheep 2.
FIG. 7, Antibody binding characteristics to various cross-reactants for antibody derived from sheep 3.

DETAILED DESCRIPTION OF THE INVENTION

The invention describes an antibody which binds to an epitope of a molecule comprising the sub-structure of structure I.

As used herein, a sub-structure represents a discernible part of a molecule (moiety) and permits additional substituents to complete the valency of each C or N where it is not evident from the structure. Specifically the N in Structure I will have two substituents, which may be the same or different, the carbons of the cyclohexyl ring of Structure I and I' may be substituted or unsubstituted by the same or different substituents, and the carbons of the phenyl ring of Structure I and II' may have one substituent which may be the same or different between the carbons.

Methoxetamine and tracer 1 of Example 10 of the General Methods, Examples and Results section, both comprise a sub-structure of structure I:

structure I or structure I':

structure I'

2-amino-2-(3-methoxyphenyl)cyclohexanone sub-structure wherein each R' is independently —H or substituted or unsubstituted alkyl. In one embodiment, one R' is —H and the other is substituted or unsubstituted alkyl $C_{1-6}$ alkyl. In one embodiment, one R' is —H and the other R' is methyl or ethyl. In one embodiment, both R' are —H.

In a preferred embodiment, the antibody binds to an epitope of a molecule comprising a sub-structure of structure II or structure II'; explicitly illustrated hydrogen atoms preclude substitution by other atoms or groups of atoms whether in chain form or constituting a ring fusion to the cyclohexyl or phenyl rings. Conversely, lack of explicitly illustrated hydrogen atoms, for example at the N linked to the cyclohexyl ring, does not preclude substitution by an atom.

structure II structure II' wherein each R' is independently —H or substituted or unsubstituted alkyl. In one embodiment, one R' is —H and the other is substituted or unsubstituted alkyl $C_{1-6}$ alkyl. In one embodiment, one R' is —H and the other R' is methyl or ethyl. In one embodiment, both R' are —H.

There are several parameters that can be used to compare the relative degree of binding of an antibody to different analytes including the lowest limit of detection, the lowest limit of quantification and the $IC_{50}$. The $IC_{50}$ is determined using a competitive assay (see Example 11 of the General Method, Examples and Results section and Table 1) and can be used to derive analyte cross-reactivities. To enable an assay to be effectively applied, an $IC_{50}$ of less than or about 50 ng/ml, preferably less than or about 20 ng/ml, more preferably less than or about 10 ng/ml or less than or about 5 ng/ml, for any individual analyte is preferred. Derivation of these parameters enables the competitive cross-reactivities of various analytes to an antibody to be determined. Competitive cross-reactivity is derived as follows (the analyte showing the greatest binding is usually given a % CCR of 100):

$IC_{50}$ analyte 1 (methoxetamine) divided by $IC_{50}$ analyte 2 (n-desmethylmethoxetamine, ketamine etc) multiplied by 100.

Thus, in a further embodiment the antibody of the invention has <5% cross-reactivity to one or more of the drugs and metabolites selected from phencyclidine, ketamine, norketamine, tilidine, tramadol, O-desmethyltramadol and N-desmethyl tramadol and >5% cross-reactivity to N-desethylmethoxetamine, each compared to 100% cross-reactivity to methoxetamine.

In another embodiment the antibody of the invention has about <15%, <10% or <5% competitive cross-reactivity to at least one of the drugs and metabolites selected from ketamine, norketamine, tramadol (including tramadol HCl), tilidine (including tilidine HCl), phencyclidine (PCP), O-desmethyltramadol (including O-desmethyl-cis-tramadol), N-desmethyl tramadol and 2-(3-methoxyphenyl) cyclohexanone and optionally about >50%, >40%, >30%, >20%, >15%, >10% or >5% competitive cross-reactivity to N-desethylmethoxetamine, compared to about 100% cross-reactivity to methoxetamine.

In another embodiment, the antibody of the invention has about <15%, <10% or <5% competitive cross-reactivity to more than one of the drugs and metabolites selected from ketamine, norketamine, tramadol (including tramadol HCl), tilidine (including tilidine HCl), phencyclidine (PCP), O-desmethyltramadol (including O-desmethyl-cis-tramadol), N-desmethyl tramadol and 2-(3-methoxyphenyl) cyclohexanone and optionally about >50%, >40%, >30%, >20%, >15%, >10% or >5% competitive cross-reactivity to N-desethylmethoxetamine, compared to about 100% cross-reactivity to methoxetamine.

In another embodiment, the antibody of the invention has about <15%, <10% or <5% competitive cross-reactivity to the drugs and metabolites selected from ketamine, norketamine, tramadol (including tramadol HCl), tilidine (including tilidine HCl), phencyclidine (PCP), O-desmethyltramadol (including O-desmethyl-cis-tramadol), N-desmethyl tramadol and 2-(3-methoxyphenyl) cyclohexanone and about >50%, >40%, >30%, >20%, >15%, >10% or >5% competitive cross-reactivity to N-desethylmethoxetamine, compared to about 100% cross-reactivity to methoxetamine.

In another embodiment, the antibody of the invention has about <5% competitive cross-reactivity to at least one of the drugs and metabolites selected from ketamine, norketamine, tramadol (including tramadol HCl), tilidine (including tilidine HCl), phencyclidine (PCP), O-desmethyltramadol (including O-desmethyl-cis-tramadol), N-desmethyl tramadol and 2-(3-methoxyphenyl) cyclohexanone and about >15% competitive cross-reactivity to N-desethylmethoxetamine, compared to about 100% cross-reactivity to methoxetamine.

In another embodiment, the antibody of the invention has about <5% competitive cross-reactivity to more than one of the drugs and metabolites selected from ketamine, norketamine, tramadol (including tramadol HCl), tilidine (including tilidine HCl), phencyclidine (PCP), O-desmethyltramadol (including O-desmethyl-cis-tramadol), N-desmethyl tramadol and 2-(3-methoxyphenyl) cyclohexanone and about >15% competitive cross-reactivity to N-desethylmethoxetamine, compared to about 100% cross-reactivity to methoxetamine.

In another embodiment, the antibody of the invention has about <5% competitive cross-reactivity to the drugs and metabolites ketamine, norketamine, tramadol (including tramadol HCl), tilidine (including tilidine HCl), phencyclidine (PCP), O-desmethyltramadol (including O-desmethyl-cis-tramadol), N-desmethyl tramadol and 2-(3-methoxyphenyl) cyclohexanone and about >15% competitive cross-reactivity to N-desethylmethoxetamine, compared to about 100% cross-reactivity to methoxetamine.

In another embodiment, the antibody of the invention has about <15%, <10% or <5% competitive cross-reactivity to ketamine and optionally about >50%, >40%, >30%, >20%, >15%, >10% or >5% competitive cross-reactivity to N-desethylmethoxetamine, compared to about 100% cross-reactivity to methoxetamine.

In another embodiment, the antibody of the invention has about <15%, <10% or <5% competitive cross-reactivity to tramadol (including tramadol HCl), and optionally about >50%, >40%, >30%, >20%, >15%, >10% or >5% competitive cross-reactivity to N-desethylmethoxetamine, compared to about 100% cross-reactivity to methoxetamine.

In another embodiment, the antibody of the invention has about <15%, <10% or <5% competitive cross-reactivity to phencyclidine (PCP), and optionally about >50%, >40%, >30%, >20%, >15%, >10% or >5% competitive cross-reactivity to N-desethylmethoxetamine, compared to about 100% cross-reactivity to methoxetamine.

In another embodiment, the antibody of the invention has about <5% competitive cross-reactivity to ketamine and optionally about >15% competitive cross-reactivity to N-desethylmethoxetamine, compared to about 100% cross-reactivity to methoxetamine.

In another embodiment, the antibody of the invention has about <5% competitive cross-reactivity to phencyclidine, and optionally about >15% competitive cross-reactivity to N-desethylmethoxetamine, compared to about 100% cross-reactivity to methoxetamine.

In another embodiment, the antibody of the invention has about <5% competitive cross-reactivity to tramadol (including tramadol HCl), and optionally about >15% competitive cross-reactivity to N-desethylmethoxetamine, compared to about 100% cross-reactivity to methoxetamine.

In one embodiment, the antibody of the invention has <5% competitive cross-reactivity to any one of ketamine, norketamine, tramadol and tilidine, optionally >15% competitive cross-reactivity to N-desethylmethoxetamine compared with a 100% competitive cross-reactivity to methoxetamine.

In one embodiment, the antibody of Claim 5 which has <5% competitive cross-reactivity to more than one of ket- amine, norketamine, tramadol and tilidine, >15% competitive cross-reactivity to N-desethylmethoxetamine compared with a 100% competitive cross-reactivity to methoxetamine.

In any of the above embodiments, the tracer can be N-(5-carboxypentyl)-N-desethylmethoxetamine-HRP.

In another embodiment the antibody of the invention has an $IC_{50}$ of about less than or about 20 ng/ml, more preferably less than or about 10 ng/ml, most preferably less than or about 1 ng/ml to methoxetamine.

Due to inter-molecular attractive forces such as hydrogen bonding and van der Waal's forces there is often a degree of binding or affinity between two molecules whatever their respective structures; the skilled person recognizes that no cross-reactivity or minimal cross-reactivity implies that in the context of a working immunoassay any binding or interaction between an antibody and non-target analytes is at such a low level that it does not compromise the integrity of the immunoassay i.e. false positives are avoided. A further embodiment of the invention is an antibody derived or raisable from an immunogen of structure III structure III wherein X is —NH— or —N(R)— in which R is substituted or unsubstituted alkyl, preferably $C_{1-6}$ alkyl, n is 0 or 1 and the accm is an antigenicity conferring carrier material. The crosslinker or crosslinking group, if present, links X to the accm and can be any appropriate acyclic or cyclic system or a combination of cyclic and acyclic systems. The crosslinker, which is standard in the art, can be a short chain saturated or unsaturated, substituted or unsubstituted alkanediyl or alkenediyl chain of 1-10 carbon atoms, or arylene groups, or saturated or unsaturated cycloalkanes, or heterocycles or combinations of alkanediyl, alkenediyl, arylene groups, saturated or unsaturated cycloalkanes and heterocycles optionally supporting a functional group (e.g. carboxy, amino, carbonyl) at the chain or ring end(s) following or preceding attachment to X and the accm. The total linear chain length of the crosslinker is preferably 1-10 atoms, most preferably 1-6 atoms. In the context of the invention, the phrase 'total linear chain length' in conjunction with 1-10 atoms or 1-6 atoms, implies that if a ring system is present in the crosslinker it is afforded the value of one atom i.e. a benzene ring and a cyclohexane ring in the crosslinker corresponds to 2 atoms and diphenylmethane (phenyl-$CH_2$-phenyl) corresponds to 3 atoms. In a preferred embodiment, the immunogen from which the antibody is derived, raisable or raised has X=—NH— and the crosslinking group is a $C_{1-10}$, preferably a $C_{1-6}$ substituted or unsubstituted alkanediyl or arylene. The immunogen from which the antibody is raised can have X=—NH—, and the crosslinking group is a $C_{1-10}$, preferably a $C_{1-6}$ substituted or unsubstituted alkanediyl or arylene moiety with a single reactive group at the end of the crosslinking group opposite to X which before attachment to the accm is a carboxy, a dithiopyridyl, a maleimido, an amino, a hydroxyl, a thiol, an ester, a thioester or formyl. In a preferred embodiment, X is —NH— and the crosslinker of structure III is —$(CH_2)_{n'}$—CO— in which n'=1-5, more preferably n'=5.

The terms "reactive group" and "functional group" are interchangeable and are standard in the chemistry field to refer to a reactive group such as an amine, ketone, ether, thioether, amide, alkene, thiol, ester, carboxylic acid or aldehyde.

Numerous accms are useable in the invention but are preferably keyhole limpet haemocyanin (KLH), bovine thyroglobulin (BTG), bovine serum albumin (BSA), egg ovalbumin, bovine gamma globulin or cationised BSA (see General Methods, Examples and Results for further examples). Antigenicity conferring carrier materials are well known in the art and can be any material that makes all or part of the hapten (the hapten is a pre-immunogenic molecule or 'small molecule'—an example in the case of the current invention is Hapten A, exemplified in Example 7 and FIG. 2) immunogenic, such as a protein, a protein fragment, a synthetic polypeptide or a semi-synthetic polypeptide.

The term "hapten" as used herein describes a pre-immunogenic molecule that stimulates antibody production only when linked to a larger carrier molecule. For the purposes of this patent application, "linked" is synonymous with bound, attached, conjugated, crosslinked, coupled, or chemically synthesised to. This larger carrier molecule can be referred to as an antigenicity-conferring carrier material (accm). Once the hapten is linked to the accm, it forms the immunogen.

The process of immunogen formation generally involves coupling of a hapten to a crosslinking agent, the latter subsequently coupled to an accm. Numerous crosslinkers and accms are commercially available and have been described in the literature (Thermo Scientific Crosslinking Technical Handbook, 1606073 April 2009; Bioconjugate Techniques G. Hermanson, ed, Academic Press, 1996, 785 pp).

The term "antibody" as used herein refers to an immunoglobulin or immunoglobulin-like molecule. In a one embodiment, the antibodies are polyclonal antibodies. However, the skilled person will understand that any type of immunoglobulin molecule or fragment thereof can be used, for example monoclonal antibodies, Fab fragments, scFv fragments and any other antigen binding fragments all of which fall within the scope of the current invention. The polyclonal antibodies may be produced by any method as known to those skilled in the art. Any suitable host animal may be used in the immunisation process including a mammalian animal for example, but not limited to, sheep, rabbit, mouse, guinea pig or horse. In addition, the antibodies may be in the form of polyclonal antisera.

The term "raisable" means that the antibody can be raised from an immunogen of the second aspect of the current invention but is not necessarily so raised. In this context, "raisable" includes, but is not limited to, "raised" and "derived".

When used in reference to an antibody, the word "specific", "specifically" or "specificity" in the context of the current invention refers to the analyte or analytes that are bound by the antibody, as gauged by a suitable metric such as the sensitivity and cross-reactivity.

The phrase "an antibody which binds or specifically binds to an epitope of structure . . . " implies that the antibody, if polyclonal, will comprise clones whose high concentration and binding characteristics ensure an assay incorporating the antibody will bind to and ultimately support the identification of the compound of interest. Alternatively, the antibody could be a monoclonal antibody specific for a particular structural part of or the whole of the compound. There are several parameters that can be used to compare the relative degree of binding to an antibody of different analytes including the lowest limit of detection, the lowest limit of quantification and the $IC_{50}$. The $IC_{50}$ can be determined using a competitive assay and can be used to derive analyte cross-reactivities.

The terms "binds", "able to bind to" or "capable of binding" as used herein means that under standard immunoassay conditions, for example as described in 'Immunoassay: A practical guide' by Brian Law, Taylor and Francis Ltd (ISBN 0-203-48349-9), the antibodies will bind to said molecules.

For purposes of comparison, one analyte with high cross-reactivity is generally given a value of 100%, with all other analytes accorded a value relative to this described herein as competitive cross-reactivity; in addition, as is known by one skilled in the art, for cross-reactivity to be of practical use the analyte specific antibody must display a high sensitivity as measured by a suitable metric such as the $IC_{50}$. The $IC_{50}$ is a commonly used indicator of antibody sensitivity for immunoassays. To enable an assay to be effectively applied in the field, an $IC_{50}$ of less than or about 5 ng/ml, less than or about 2.5 ng/ml, less than or about 2.0 ng/ml, and or less than about 1.0 ng/ml for any individual analyte. Given the $IC_{50}$ of various analytes, their cross-reactivities, often represented as relative percentages, can be calculated.

The term "alkyl" as used herein means a saturated straight or branched chain hydrocarbon.

The term "alkenyl" as used herein means a straight or branched chain hydrocarbon comprising one or more double bonds. The term "alkynyl" as used herein means a straight or branched chain hydrocarbon comprising one or more triple bonds. Each of the "alkyl", "alkenyl" or "alkynyl" as used herein can be optionally substituted as set forth below. In some embodiments, the "alkyl" is $C_{1-6}$ alkyl or $C_{1-4}$ alkyl. In some embodiments, the "alkenyl" is $C_{2-6}$ alkenyl or $C_{2-4}$ alkenyl. In some embodiments, the "alkynyl" is $C_{2-6}$ alkynyl or $C_{2-4}$ alkynyl. The terms "alkylene," and "alkanediyl" can be used interchangeably and represent a saturated divalent straight or branched chain alkyl group and is exemplified by methylene, ethylene, isopropylene and the like.

The term "alkenediyl" represents an unsaturated divalent straight or branched chain alkene group.

The term "arylene" represents an unsaturated divalent straight or branched chain hydrocarbon group containing at least one double bond.

The term "cycloaliphatic" (or "carbocycle" or "carbocyclyl" or "carbocyclic") refers to a non-aromatic carbon only containing ring system which can be saturated or contains one or more units of unsaturation, having three to fourteen ring carbon atoms. In some embodiments, the number of carbon atoms is 3 to 10. In other embodiments, the number of carbon atoms is 4 to 7. In yet other embodiments, the number of carbon atoms is 5 or 6. The term includes monocyclic, bicyclic or polycyclic, fused, spiro or bridged carbocyclic ring systems. The term also includes polycyclic ring systems in which the carbocyclic ring can be "fused" to one or more non-aromatic carbocyclic or heterocyclic rings or one or more aromatic rings or combination thereof, wherein the radical or point of attachment is on the carbocyclic ring. "Fused" bicyclic ring systems comprise two rings which share two adjoining ring atoms. Bridged bicyclic group comprise two rings which share three or four adjacent ring atoms. Spiro bicyclic ring systems share one ring atom. Examples of cycloaliphatic groups include, but are not limited to, cycloalkyl and cycloalkenyl groups. Specific examples include, but are not limited to, cyclohexyl, cyclopropenyl, and cyclobutyl. The terms "cycloalkane" and "cycloalkyl" can be used interchangeably.

The term "heterocycle" (or "heterocyclyl", or "heterocyclic" or "non-aromatic heterocycle") as used herein refers to a non-aromatic ring system which can be saturated or contain one or more units of unsaturation, having three to fourteen ring atoms in which one or more ring carbons is replaced by a heteroatom such as, N, S, or O and each ring in the system contains 3 to 7 members. In some embodiments, non-aromatic heterocyclic rings comprise up to three heteroatoms selected from N, S and O within the ring. In other embodiments, non-aromatic heterocyclic rings comprise up to two heteroatoms selected from N, S and O within the ring system. In yet other embodiments, non-aromatic heterocyclic rings comprise up to two heteroatoms selected from N and O within the ring system. The term includes monocyclic, bicyclic or polycyclic fused, spiro or bridged heterocyclic ring systems. The term also includes polycyclic ring systems in which the heterocyclic ring can be fused to one or more non-aromatic carbocyclic or heterocyclic rings or one or more aromatic rings or combination thereof, wherein the radical or point of attachment is on the heterocyclic ring. Examples of heterocycles include, but are not limited to, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, thiazocanyl, benzimidazolonyl, tetrahydrofuranyl, tetrahydrofuranyl, tetrahydrothiophenyl, tetrahydrothiophenyl, morpholino, including, for example, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolanyl, benzodithianyl, 3-(1-alkyl)-benzimidazol-2-onyl, and 1,3-dihydro-imidazol-2-onyl.

The term "aryl" (or "aryl ring" or "aryl group") used alone or as part of a larger moiety as in "aralkyl", "aralkoxy", "aryloxyalkyl", or "heteroaryl" refers to carbocyclic aromatic ring systems. The term "aryl" may be used interchangeably with the terms "aryl ring" or "aryl group".

The term "arylene" is a divalent aryl group as defined above.

"Carbocyclic aromatic ring" groups have only carbon ring atoms (typically six to fourteen) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term "carbocyclic aromatic ring" or "carbocyclic aromatic", as it is used herein, is a group in which an aromatic ring is "fused" to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The terms "heteroaryl", "heteroaromatic", "heteroaryl ring", "heteroaryl group", "aromatic heterocycle" or "heteroaromatic group", used alone or as part of a larger moiety as in "heteroaralkyl" or "heteroarylalkoxy", refer to heteroaromatic ring groups having five to fourteen members, including monocyclic heteroaromatic rings and polycyclic aromatic rings in which a monocyclic aromatic ring is fused to one or more other aromatic ring. Heteroaryl groups have one or more ring heteroatoms. Also included within the scope of the term "heteroaryl", as it is used herein, is a group in which an aromatic ring is "fused" to one or more non-aromatic rings (carbocyclic or heterocyclic), where the radical or point of attachment is on the aromatic ring. Bicyclic 6,5 heteroaromatic ring, as used herein, for example, is a six membered heteroaromatic ring fused to a second five membered ring, wherein the radical or point of attachment is on the six membered ring. Examples of heteroaryl groups include pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As described herein, compounds of the invention may optionally be substituted with one or more substituents, such as illustrated generally below, or as exemplified by particular species of the invention. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, (for example in Structure II and II' where the hydrogens are specifically exemplified) an optionally substituted group may have a substituent at each substitutable position of the group. When more than one position in a given structure can be substituted with more than one substituent selected from a specified group, the substituent may be either the same or different at each position. When the term "optionally substituted" precedes a list, said term refers to all of the subsequent substitutable groups in that list.

Selection of substituents and combinations of substituents envisioned by this invention are those that result in the formation of stable or chemically feasible compounds. The term "stable", as used herein, refers to compounds that are not substantially altered when subjected to conditions to allow for their production, detection, and, specifically, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. Only those choices and combinations of substituents that result in a stable structure are contemplated. Such choices and combinations will be apparent to those of ordinary skill in the art and may be determined without undue experimentation.

The terms "saturated" as used herein implies that absence of double or triple bonds, the "unsaturated" implies the presence of at least one double or triple bond.

Suitable substituents on a saturated or unsaturated carbon or nitrogen are $C_{1-6}$ alkyl, halogen, cyano, oxo, —NCO, —OR$^b$, —SR$^b$, —S(O)R$^a$, —SO$_2$R$^a$, —NR$^b$R$^c$, —C(O)R$^b$, —C(O)OR$^b$, —OC(O)R$^b$, —NRC(O)R$^b$, —C(O)NR$^b$R$^c$, —NR$^b$C(O)NR$^b$R$^c$, —NR$^b$C(O)OR$^b$, —OCONR$^b$R$^c$, —C(O)NRCO$_2$R$^b$, —NR$^b$C(O)NR$^b$C(O)OR$^b$, —C(O)NR(OR$^b$), —SO$_2$NR$^c$R$^b$, —NR$^b$SO$_2$R$^b$, —NR$^b$SO$_2$NR$^c$R$^b$, or —P(O)(OR$^a$)$_2$—; or two substituents join together with the atoms to which they are attached to form a 5-7-membered cycloalkyl or heterocyclic ring. Each R$^a$, R$^b$ and R$^c$ are each independently —H or $C_{1-6}$ alkyl. Other suitable substituents for a saturated carbon include the following: =O, =S, =NNHR*, =NN(R*)$_2$, =NNHC(O)R*, =NNHCO$_2$(alkyl), =NNHSO$_2$(alkyl), or =NR*, wherein each R* is independently selected from —H or $C_1$-$C_6$ alkyl.

Unless otherwise indicated, structures depicted herein are also meant to include all isomeric (e.g., enantiomeric, diastereomeric, cis-trans, conformational, and rotational) forms of the structure. For example, the R and S configurations for each asymmetric centre, (Z) and (E) double bond isomers, and (Z) and (E) conformational isomers are included in this invention, unless only one of the isomers is drawn specifically. As would be understood to one skilled in the art, a substituent can freely rotate around any rotatable bonds. Therefore, single stereochemical isomers as well as enantiomeric, diastereomeric, cis/trans, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays. Such compounds, especially deuterium analogues, can also be therapeutically useful.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The invention further describes an immunoassay method of detecting or determining methoxetamine in an in vitro sample or in a solution comprising contacting the sample or solution with a detecting agent (also called a 'tracer' or 'conjugate') and an antibody of the invention, detecting the bound detecting agent and deducing the presence or amount of methoxetamine. By 'detecting' is meant qualitatively analysing for the presence or absence of a substance; by 'determining' is meant quantitatively analysing for the amount of a substance present. The detection or determination step is usually effected with the aid of a calibrator.

A calibrator is well known in the art and enables a threshold concentration or the exact or calibrator equivalent amount of an analyte to be determined. A calibrator curve or threshold concentration may be suitable for several analytes or may have to be derived for each individual analyte. The determination of an exact or calibrator equivalent amount of an analyte often requires the construction of a calibration curve (also known as a standard curve). The number of calibrator points can vary, but is usually from 5 to 9.

The in vitro sample is any suitable biological sample such as, but not limited to, blood, serum, plasma, urine or saliva. The in vitro sample is preferably a serum, plasma or urine sample. The solution can be a liquid suspected of containing methoxetamine. Alternatively, as methoxetamine is often in solid form, analysis may require pre-treatment to achieve a formulation suitable for immunoanalysis, such as dissolution in a suitable liquid. The term "biological sample", as used herein, includes, without limitation, cell cultures or extracts thereof; biopsied material obtained from a mammal or extracts thereof; blood, saliva, urine, faeces, semen, tears, or other body fluids or extracts thereof. In one embodiment, the biological sample is a peripheral biological fluid, but is including whole blood, serum, plasma, hair or urine. The sample may also be a solution which is suspected of containing a drug.

The immunoassay method is preferably based on the well-known competitive assay format in which a target analyte which binds to the antibody i.e. the molecule to be detected or determined, competes with a detecting agent which also binds to the antibody, for binding sites on the antibody. The detecting agent can be any substance which leads to a detectable or measurable signal and typically incorporates an enzyme which promotes light emission from a substrate, a fluorophore or a radioactive label; it is usual for an immunoassay that the detecting agent incorporates a structure similar to the target analyte to which an enzyme or a substance having fluorescent properties has been conjugated, or in which a radiolabel has been incorporated. Preferably, for the immunoassay method of the invention, the detecting agent is based on a compound with substructure II. Conjugation is by way of standard methods familiar to the skilled person and may involve the crosslinking methodology and groups described previously for the immunogen of the invention. Examples of detecting agents and their syntheses are described the General Methods, Examples and Results section. The 'detecting and determining' criteria for the immunoassay method includes, as is well-known in the art, exceeding a pre-defined cut-off/ concentration value or measuring the calibrator equivalent value as derived from a calibrator curve (also referred to as a standard curve). In a preferred embodiment the detecting agent (also called a 'tracer' or 'conjugate') is structure IV structure IV In which Y is —X'-(crosslinker)$_n$- and links the detectable label to the cyclohexyl ring, wherein X', attached to the cyclohexyl ring, is —N—, —O— or —S— and is attached to the detectable label optionally by way of a crosslinking group i.e. n=0 or 1. The possible crosslinking groups for the detecting agent are as described for the crosslinking group for the immunogen used in the immunoassay method of the invention; preferably, the crosslinker of the detecting agent is —(CH$_2$)$_{n'}$—CO— in which n'=1-5, more preferably n'=5. The detectable label can be any structure which enables detection or measurement of the detecting agent such as an enzyme or a substance having fluorescent properties; preferably, the detectable label of the invention is horseradish peroxidase (HRP) and Y is —(CH$_2$)$_{n'}$—CO— in which n'=1-5, more preferably n'=5. The current invention in all its aspects also refers to individual stereoconfigurations, enantiomers of methoxetamine and its metabolites, as well as mixtures of enantiomers including racemic mixtures.

The invention further describes a kit comprising an antibody of the invention and optionally a detecting agent of the invention which is preferably of structure IV. The kit can also be presented with the antibodies passively adsorbed on or chemically bonded to a solid state device. A solid state device may also be referred to as a substrate.

Another aspect of the invention is a substrate which supports the antibodies of the invention. The antibodies engage with the substrate by, for example, passive adsorption or can be chemically bonded to the substrate attached by way of, for example, covalent bonds. Such covalent bonding generally requires the initial introduction of a chemically active compound covalently attached to the substrate surface prior to antibody addition. The antibody itself may also require the addition of a chemical activating group to achieve substrate bonding. These requirements are well known in the art. The substrate can be any medium capable of adsorbing or bonding to an antibody, for example a bead, a microtitre plate or a nanoparticle (optionally chemically-activated), but is preferably of a planar conformation (optionally chemically-activated) such as a glass slide or a biochip. A biochip or a microtitre plate are the preferred substrates. A biochip is a thin, wafer-like substrate with a planar surface which can be made of any suitable material such as glass or plastic but is preferably made of ceramic. The biochip is able to be chemically-activated prior to antibody bonding or is amenable to the passive adsorption of antibodies. The skilled person in biochip development for immunoassay application will recognize that a planar surface at high resolution e.g. if using a scanning electron microscope, is not perfectly 'flat' but will possess an uneven surface, the important aspect being that the 'approximately' planar surface is suitable for application. A microlayer coating of material can optionally be added to the planar surface of the substrate prior to antibody placement. Either the upper surface or both surfaces of the substrate can be coated. The biochip can be integrated into or placed into a device with walls. Such a walled device can aid in the retention of added sample or solution. The solid state device can also support other antibodies which have a binding specificity which is different from the binding specificity of the antibodies of the invention. Such a support with multiple different antibodies is often described as a multianalyte array (reference to an 'array' includes a microarray). If the method of detection is different fluorescent labels, each different fluorescent label emitting electromagnetic radiation at a unique wavelength, then the location of placement of the antibodies on the solid substrate is not critical. However, for antibodies forming part of a multianalyte array in which the detecting agent is, for example, a chemiluminescent molecule, the antibodies of differing specificity must not overlap and must be located in discrete areas on the solid state device. Such a system is also referred to as a spatially addressable multianalyte array.

Figure 1:
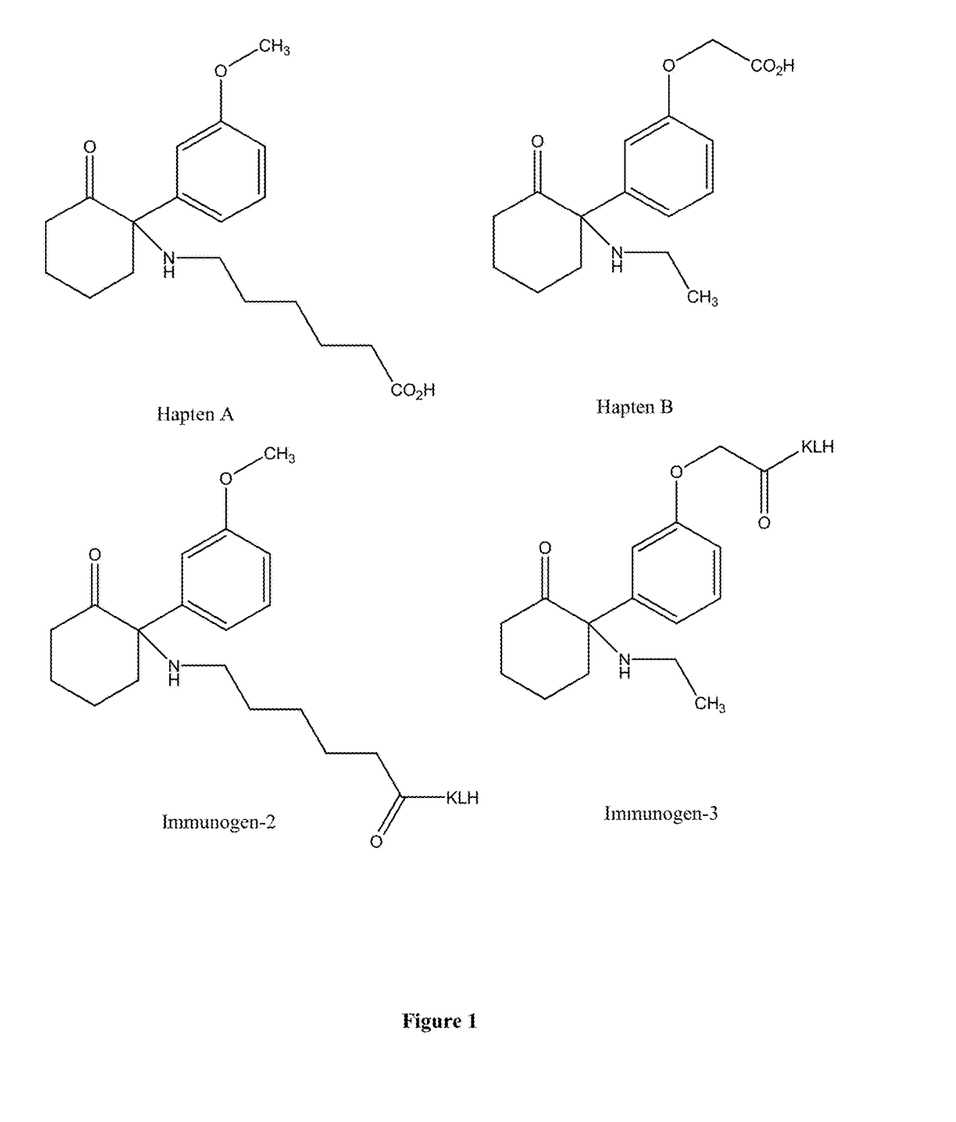
FIG. 1, Methoxetamine haptens and immunogens.

The invention also describes an immunogen of structure III (as previously described), wherein X is —NH— or —N(R)— in which R is substituted or unsubstituted alkyl, preferably $C_{1-6}$ alkyl, n is 0 or 1 and the accm is an antigenicity conferring carrier material. The crosslinker or crosslinking group, if present, links X to the accm and can be any appropriate acyclic or cyclic system or a combination of cyclic and acyclic systems. The crosslinker can be a short chain saturated or unsaturated, substituted or unsubstituted alkanediyl or alkenediyl chain of 1-10 carbon atoms, or arylene groups, or saturated or unsaturated cycloalkanes, or heterocycles or combinations of alkanediyl, alkenediyl, arylene groups, saturated or unsaturated cycloalkanes and heterocycles optionally supporting a functional group (e.g. carboxy, amino, carbonyl) at the chain or ring end(s) following or preceding attachment to X and the accm. The total linear chain length of the crosslinker is preferably 1-10 atoms. In a preferred embodiment, the immunogen from which the antibody is raised has X═—NH— and the crosslinking group is a $C_{1-10}$, preferably a $C_{1-6}$ substituted or unsubstituted alkanediyl or arylene. The immunogen from which the antibody is raised can have X═—NH—, and the crosslinking group is a $C_{1-10}$, preferably a $C_{1-6}$ substituted or unsubstituted alkanediyl or arylene moiety with a single reactive group at the end of the crosslinking group opposite to X which before attachment to the accm is a carboxy, a dithiopyridyl, a maleimido, an amino, a hydroxyl, a thiol, an ester, a thioester or formyl. In a preferred embodiment, X is —NH— and the crosslinker is —$(CH_2)_{n'}$—CO— in which n'=1-5, more preferably n'=5. Accms useable in the invention include keyhole limpet haemocyanin (KLH), bovine thyroglobulin (BTG), bovine serum albumin (BSA), egg ovalbumin, bovine gamma globulin or cationised BSA (see General Methods, Examples and Results for further examples). In a preferred embodiment the immunogen is immunogen-2 of FIG. 1.

Enzyme Immunoassays, ELISAs

The enzyme-linked immunosorbent assay (ELISA) is a test that uses antibodies and colour change to identify a substance.

Antigens from the sample are attached to a surface. Then, a further specific antibody is applied over the surface so it can bind to the antigen. This antibody is linked to an enzyme, and, in the final step, a substance containing the enzyme's substrate is added. The subsequent reaction produces a detectable signal, most commonly a colour change in the substrate.

Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bioconjugation. Between each step, the plate is typically washed to remove any proteins or antibodies that are not specifically bound. After the final wash step, the plate is developed by adding an enzymatic substrate to produce a visible signal, which indicates the quantity of antigen in the sample.

Lateral Flow Devices

In recent years, the in vitro diagnostics industry has made enormous efforts to develop immunochromatographic tests. Such tests have found applications in both clinical and non-clinical fields. A clinical utility of this test format is particularly suited to point of care utilities.

Rapid immunochromatographic test devices, e.g. in the form of a test strip, are made up of a number of components. Such a test strip commonly includes a sample pad, a conjugate pad, a membrane, e.g. a nitrocellulose membrane, and an absorbent pad. The membrane is usually attached by means of an adhesive to a supporting backing, e.g. made of plastic. In practice, the user dispenses a patient sample (such as urine or whole blood) onto the sample pad. The sample then flows through the sample pad into the conjugate pad, where it mixes with, and releases, the detector reagent. This mixture then flows across the membrane, where it binds with the test and control reagents located in the capture test zone (sample zone) and negative control zone, respectively. When the mixture binds to the reagent that forms the test line, a positive result is indicated. The colour intensity of the test line is proportional to the concentration of analyte in the sample. Excess sample that flows beyond the test and control zones is taken up in the absorbent pad. Rapid immunochromatographic test devices for diagnostic purposes are easy to operate and thus do not only contribute to the comfort of professional users, e.g. medical stuff, but also allow the operation by non-professionals users, e.g. most patients.

Biochips

Biochips are components used for example in chemical analysis (including Proteomic and Molecular analysis) either to host a test reaction and/or to supply samples under test or reagents. Generally, a Biochip comprises a solid substrate, on which is arranged one or more test sites at which a reaction can take place in use. For instance, the test site may carry one or more reagents (e.g. ligands such as antibodies or antigens) adsorbed to the substrate, which are activated by the addition of a sample substance (e.g. analytes present in the sample bind to specific ligands). Such chips are sometimes referred to as a "lab on a chip" and can also incorporate tools for controlling steps of a reaction. As an example, one Biochip supplied by Randox Laboratories Limited (55 Diamond Road, Crumlin, County Antrim, United Kingdom, BT29 4QY) is used as a medium for performing multiplex analysis of biological samples using a chemiluminescence method. In this example, the Biochip takes the form of a small ceramic chip with a specialised surface preparation which is sensitive to environmental degradation. Therefore the Biochip is generally delivered in an environmentally sealed format, usually evacuated, sealed foil bags.

For instance, the Evidence™ analyser by Randox Laboratories Ltd uses biochips which are fitted into a plastic holder defining three recesses arranged in a line. Each recess is approximately square and sized to just accommodate a biochip, which is also square, with a small clearance to allow the chip to be placed. The "strip" of three mounted biochips is placed within a sealed foil bag for storage, which is then opened when the biochips are required for use. The plastic holder may be placed on a carrier alongside two further strips of three biochips to form a 3×3 array of biochips. The carrier has a keying feature for engagement with a robotic arm such that the array can be transported within the analyser via robotic handling. This configuration is useful for batch analysis.

A "Biochip" is a general term for a reaction platform for hosting chemical, biochemical, proteomic or molecular tests, as may be required for medical diagnosis, drug detection, etc. Typically, a Biochip comprises an inert substrate, such as silicon or glass (often of the order of about 1 cm$^2$ or less in surface area), on which one or a plurality of reaction sites is provided. The sites generally carry one or more ligands, for example, one or more antibodies, selected for the test (or "assay") to be performed, adsorbed to the surface of the chip for activation upon combination with a sample applied to the chip (e.g. a blood sample) and/or a reagent. The reactions can be detected using a number of alternative techniques, including detection of chemiluminescence generated by the reaction. Some biochips carry a very large number (hundreds or thousands) of such tests sites, typically arranged in a grid or array, making it possible to carry out numerous assays simultaneously, and using the same single specimen.

General Methods, Examples and Results
Preparation of Haptens, Immunogens and Detecting Agents In immunology, haptens are defined as substances which by themselves cannot elicit immune responses; they require chemical coupling to larger immunogenic molecules (antigenicity conferring carrier materials or 'accm'), to be capable of inducing an immune response.

Appropriate accms commonly contain poly(amino acid) segments and include polypeptides, proteins and protein fragments. Illustrative examples of antigencity conferring carrier materials are keyhole limpet haemocyanin (KLH), bovine thyroglobulin (BTG), bovine serum albumin (BSA), egg ovalbumin, bovine gamma globulin or cationised BSA. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen. The haptens can also be coupled to a detectable labelling agent such as an enzyme (for example, horseradish peroxidase), a substance having fluorescent properties or a radioactive label for the preparation of detecting agents for use in the immunoassays. The fluorescent substance may be, for example, a monovalent residue of fluorescein or a derivative thereof. Conjugation of haptens can be performed using standard methods of conjugation such as mixed anhydride, EDC or succinimidyl activation of the haptens. In order to confirm that adequate conjugation of hapten to carrier material has been achieved, prior to immunisation, each immunogen is evaluated using matrix-assisted UV laser desorption/ionisation time-of-flight mass spectroscopy (MALDI-TOF MS).

General Procedure for MALDI-TOF Analysis of Immunogens

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of sinapinic acid and bovine serum albumin (Fluka) was used as an external calibrant.

Preparation of Antisera

Pre-immunization blood samples are collected from sheep. In order to generate polyclonal antisera, 2 mgs of the immunogen is prepared in PBS, mixed at a ratio of 50% immunogen in PBS to 50% Freund's Complete adjuvant (Sigma, Product Number F5881) and emulsified by repeatedly passing the mixture through a tip on the end of a 1 ml syringe, until it reaches the required semi-solid consistency. 1.1 ml of the emulsified mixture is injected intramuscularly into each host animal (sheep) as the primary immunisation dose. Further injections (boosts) are prepared (1 mg of immunogen is prepared in PBS and mixed at a ratio of 50% Immunogen in PBS/50% Freunds Incomplete adjuvant, Sigma, Product Number—F5506). Boost injections are delivered intramuscularly at monthly intervals, 1 ml per animal. Serum is sampled monthly by collection of whole blood from the jugular vein for evaluation of the antibody titre. The degree of antibody purification required depends on the intended application. For many purposes, there is no requirement for purification of the serum, however, in other cases, such as where the antibody is to be immobilised on a solid support, purification steps (such as caprylic acid/ ammonium sulphate precipitation) can be taken to remove undesired material and eliminate non-specific binding. In one embodiment, the purification is by immunoglobulin precipitation, antigen-specific affinity purification, column chromatography, such as, size-exclusion chromatography or ion exchange chromatography.

Immunoassay Development

The process of developing an immunoassay is well known to the person skilled in the art. A detecting agent (e.g. appropriate hapten conjugated to HRP) is added to a sample containing the target analyte and the raised antibodies, and the detecting agent and analyte compete for binding to the antibodies. The said antibodies were fixed to a polystyrene solid support (e.g. dilution of antibodies in coating buffer and incubation at 37° C. for 2 hours to allow antibody binding to surface). The antibodies can be polyclonal or monoclonal using standard techniques, but the current invention makes use of polyclonal antibodies. The signal emitted in the immunoassay is proportionate to the amount of detecting agent bound to the antibodies which in turn is inversely proportionate to the analyte concentration. The signal can be detected or quantified by comparison with a calibrator with known levels of target analyte.

Figure 2:
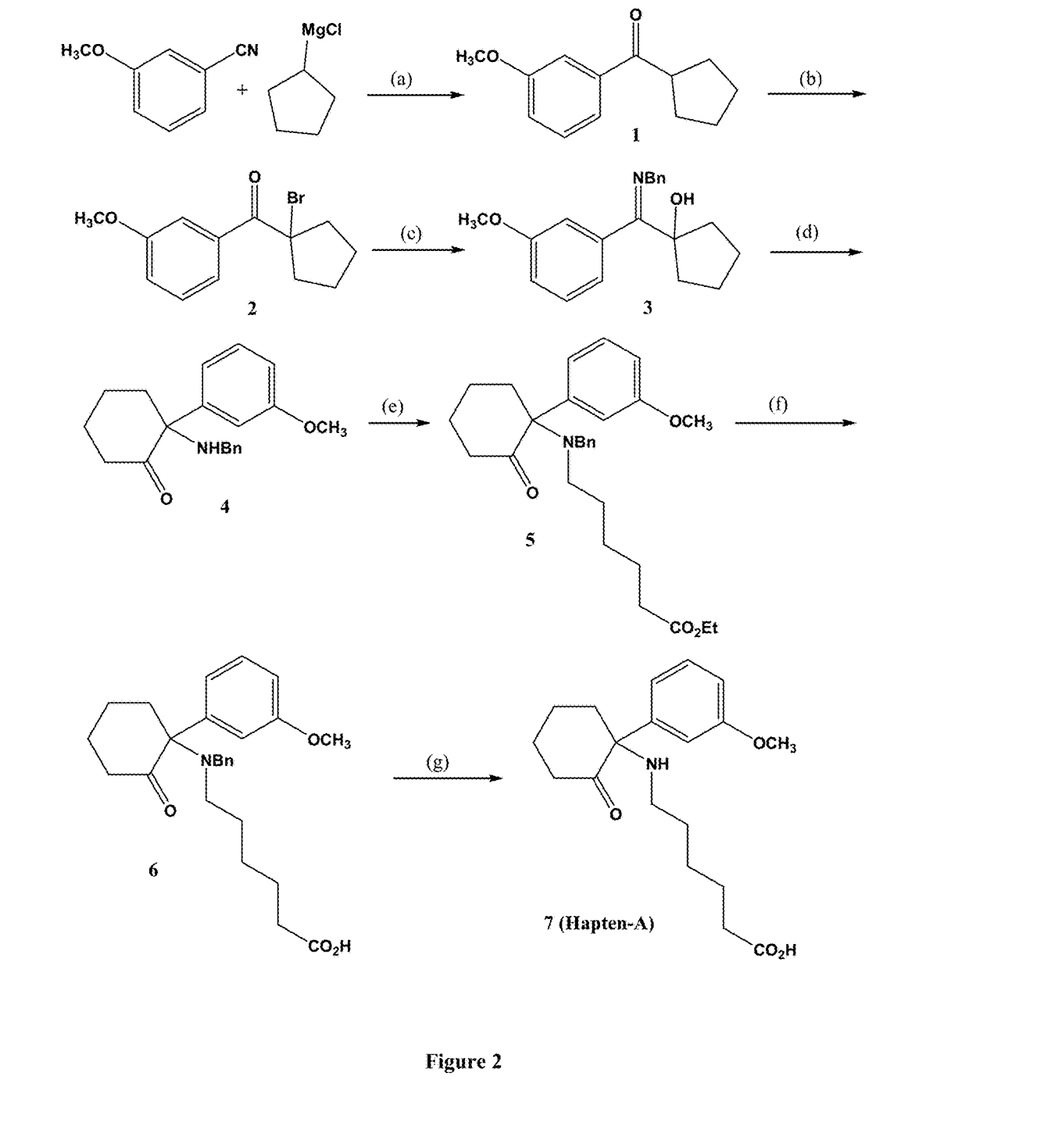
FIG. 2, Synthesis of Hapten A.
Figure 3:
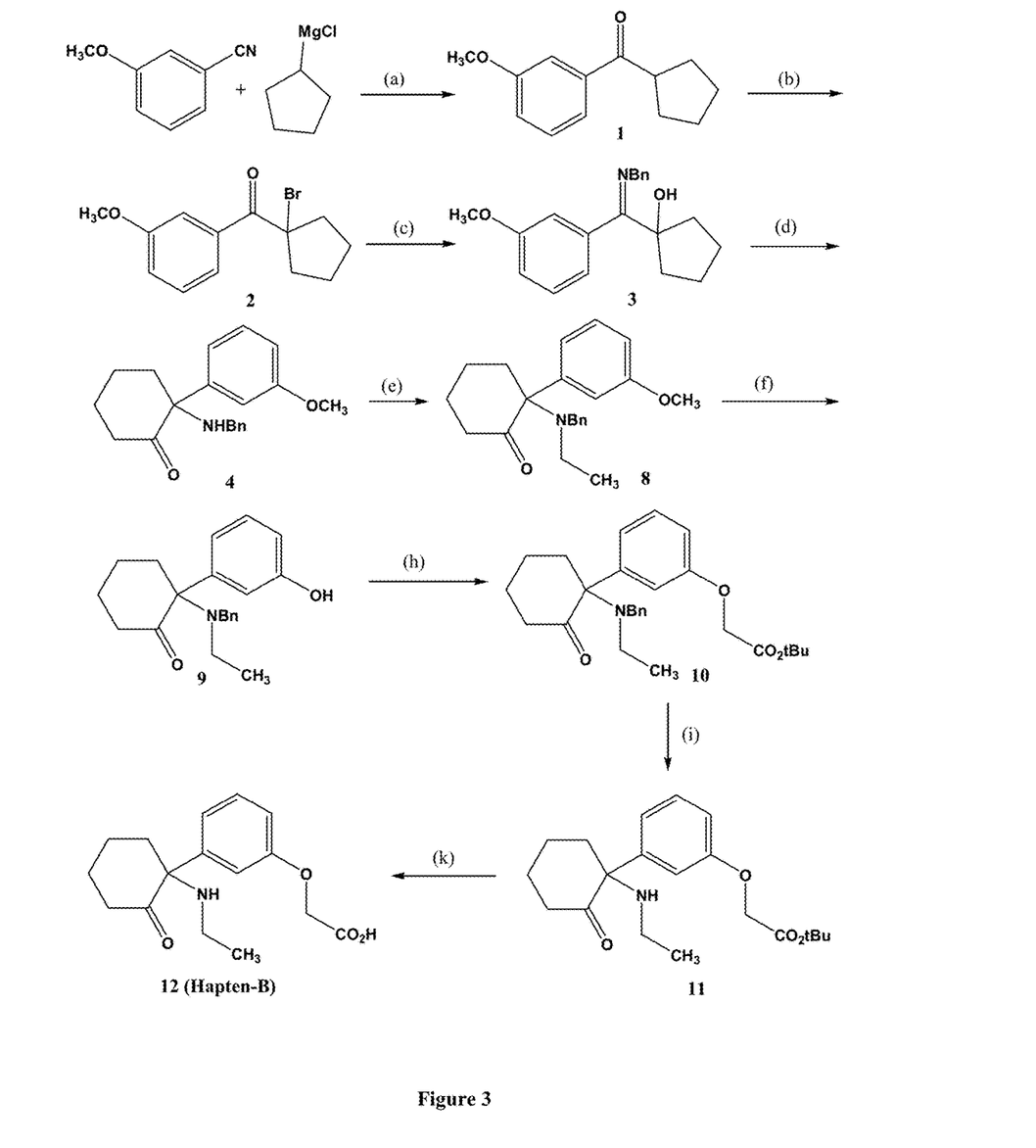
FIG. 3, Synthesis of Hapten B.
Figure 4:
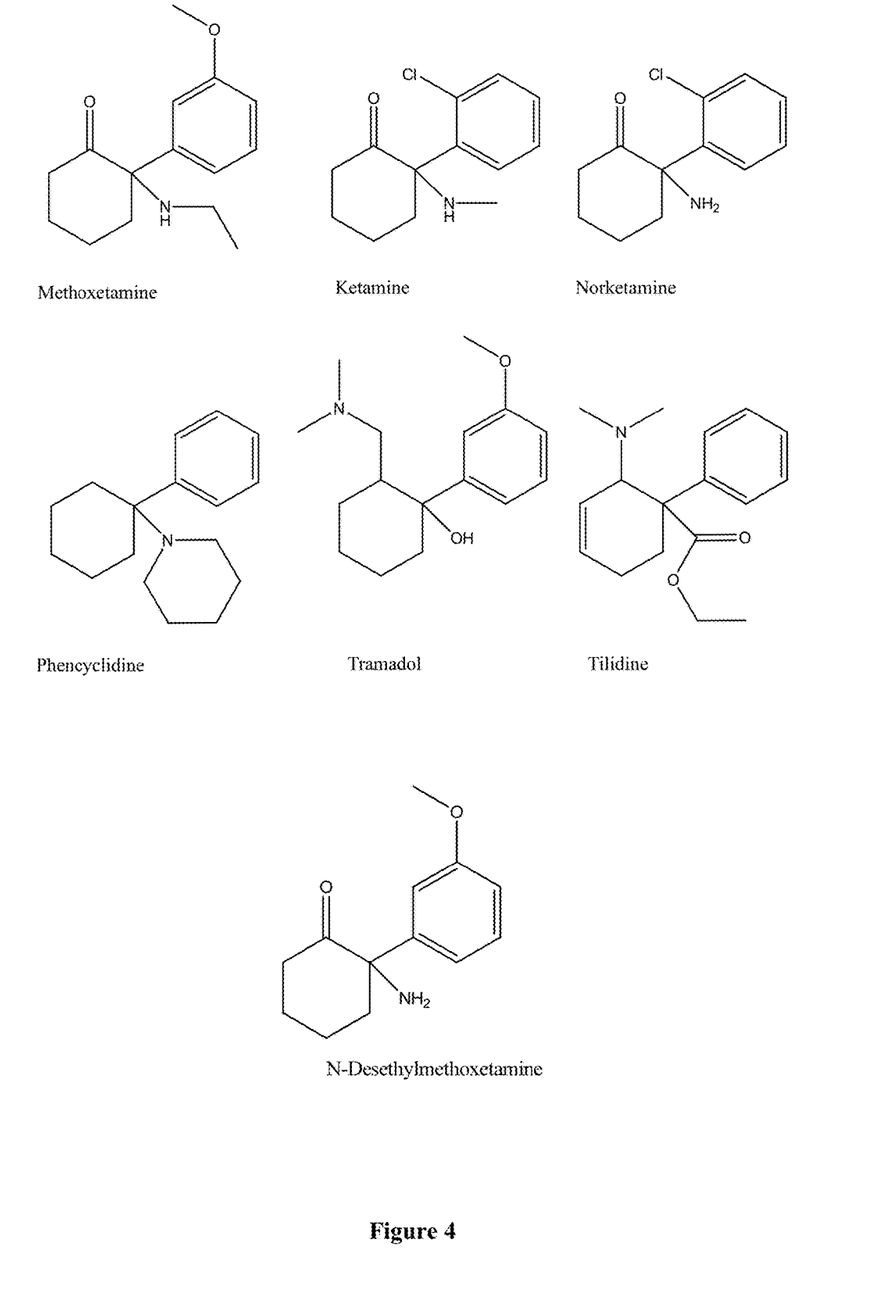
FIG. 4, Chemical structures of methoxetamine, N-desethyl methoxetamine and structurally related drugs.

Example 1: Synthesis of (m-methoxyphenyl)cyclopentyl ketone 1 (FIG. 2)

To a cooled solution at 0° C. of cyclopropyl magnesium bromide 2M in diethyl ether under nitrogen (119.41 ml, 0.238 mol) was added dropwise a solution 3-methoxybenzonitrile (30 g, 0.225 mol) in diethyl ether (50 ml) and the mixture was stirred at room temperature overnight. TLC 10% ethyl acetate in hexane shows completion of the reaction. The reaction is then hydrolysed by pouring it onto a mixture of crushed ice and ammonium chloride and the mixture was stirred until all the salts dissolve and the mixture was then extracted with ethyl acetate (3×150 ml). The combined organic layers where washed by water (150 ml), brine (150 ml), dried over sodium sulphate and concentrate to dryness. The crude mixture obtained was purified by chromatography on silica gel (10% ethyl acetate in hexane) to give a yellow oil (m-methoxyphenyl)cyclopentyl ketone 1 (25.0 g).

Example 2: Synthesis of 1-bromocyclopentyl (m-methoxyphenyl) ketone 2 (FIG. 2)

To a cooled solution 0° C. of (m-methoxyphenyl)cyclopentyl ketone 1 (22 g, 0.107 mol) in carbon tetrachloride (100 ml) was added dropwise a bromine solution (5.54 ml, 0.107 mol) in carbon tetrachloride (50 ml) and the mixture was stirred at 0° C. for 30 minutes and at room temperature for 30 minutes. Chloroform (200 ml) was added and the mixture was washed with 10% sodium thiosulfate (3×100 ml), brine (200 ml), dried over sodium sulphate, filtered and evaporated to dryness to give the title compound 1-bromo-cyclopentyl (m-methoxyphenyl) ketone 2 (30.1 g) as a brine oil used in the next step without further.

Example 3: Synthesis of 1-(alpha-benzylimino) (m-methoxybenzyl) cyclopentanol 3 (FIG. 2)

A solution containing 1-bromocyclopentyl (m-methoxyphenyl) ketone 2 (30.1 g. 0.106 mol) in benzene (100 m and benzylamine (57 g, 0.532 mol) was stirred at room temperature for 5 days. Then n-pentane was added and the reaction mixture was filtered, evaporated and concentrated to dryness. The obtained brown oily residue was chromatographed on silica gel column using 10% ethyl acetate in hexane to give 1-(alpha-benzylimino) (m-methoxybenzyl) cyclopentanol 3 (18.0 g).

Example 4: Synthesis of 2-(benzylamino)-2-(m-methoxyphenyl)cyclohexanone 4 (FIG. 2)

A solution containing 1-(alpha-benzylimino) (m-methoxybenzyl) cyclopentanol 3 (9.78 g, 0.033 mol) in Dowtherm™ (60 ml) was heated at 200° C. for 1 hour and stirred at room temperature for 6 hours. Diethyl ether was added to the solution and the mixture was extracted with (0.1M) HCl. The aqueous layer was basified with (1M) NaOH and extracted with ethyl acetate several times. The combined organic layers were washed with brine, dried over sodium sulphate, filtered and the solvent was removed under vacuo. The residue was purified on column chromatography (silica gel, 0-10-20% EtOAc in hexane) to give 2.93 g of 2-(benzylamino)-2-(m-methoxyphenyl)cyclohexanone 4.
NMR 13C (DMSOd6: δ ppm): 210.6, 159.7, 142.51, 141.52, 129.79, 128.4, 128.15, 126.84, 119.92, 113.61, 112.44, 79.89, 69.81, 55.35, 46.64, 38.06, 27.44, 21.83.

Example 5: Synthesis of 2-[N-benzyl-N-(6-ethoxy-6-oxo-hexyl)]-2-(m-methoxyphenyl) cyclohexanone 5 (FIG. 2)

To a solution of 2-(benzylamino)-2-(m-methoxyphenyl) cyclohexanone 4 (790 mg, 2.55 mmol) in 1, 2-dichloroethane (10 ml) was added a solution of ethyl 6-oxohexanoate (444.3 mg, 2.8 mmol) in 1, 2-dichloroethane (10 ml). The reaction mixture was stirred at room temperature for 10 minutes was added one drop of acetic acid followed by the addition sodium triacetoxyborohydride (811 mgs, 1.5 eq). The reaction mixture was stirred at room temperature overnight. A saturated solution of sodium bicarbonate was added and the resulting mixture was stirred at room temperature for 30 min. The layers were separated and the aqueous layer was extracted with chloroform (3×25 ml). The combined organic layers were washed with brine, dried over sodium sulphate, filtered and the solvent was removed under vacuo. The residue was purified on column chromatography (silica gel, 10-20% ethyl acetate in hexane) to give 2-[N-benzyl-N-(6-ethoxy-6-oxo-hexyl)]-2-(m-methoxyphenyl) cyclohexanone 5 (342 mgs).

Example 6: Synthesis 2-[N-benzyl-N-(5-carboxypentyl)]-2-(m-methoxyphenyl) cyclohexanone 6 (FIG. 2)

To a solution of 2-[N-benzyl-N-(6-ethoxy-6-oxo-hexyl)]-2-(m-methoxyphenyl) cyclohexanone 5 (342 mgs, 0.75 mmol) in tetrahydrofuran (10 ml) was added dropwise a solution of lithium hydroxide monohydrate (95.3 mg, 2.27 mmol) in water (10 ml). The reaction mixture was stirred at room temperature overnight. The reaction mixture was neutralised to pH 7 by the addition of (3M) HCl and the solution was concentrated to dryness. Water was then added to the residue and the aqueous solution was extracted with ethyl acetate (3×25 ml). The combined organic layers were dried over sodium sulphate, filtered and the solvent evaporated to give 2-[N-benzyl-N-(5-carboxypentyl)]-2-(m-methoxyphenyl) cyclohexanone 6 (281 mg).

Example 7: Synthesis of N-(5-carboxypentyl)-N-desethylmethoxetamine 7 (Hapten-A) (FIG. 2)

To a solution of 2-[N-benzyl-N-(5-carboxypentyl)]-2-(m-methoxyphenyl)cyclohexanone 6 (281 mg, 0.66 mmol) in 10 ml ethanol was added Pd/C 5% (281 mg) and hydrogen gas was bubbled in the reaction mixture at room temperature until the TLC showed the completion of reaction (no starting material left). The reaction mixture was filtered through a pad of celite and the solution was evaporated to dryness. The residue obtained was purified by column chromatography (silica gel, 10% methanol in chloroform) to give N-(5-carboxypentyl)-N-desethylmethoxetamine 7 (Hapten-A) (187 mg).
NMR13C (DMSOd6; δ ppm): 210.07, 174.43, 159.19, 129.18, 119.43, 113.12 (2), 111.8, 69.07, 54.93, 41.79, 37.66, 33.6, 30.6, 29.74, 29.57, 26.7, 26.29, 24.37, 21.34, Example 8: Conjugation of N-(5-carboxypentyl)-N-desethylmethoxetamine 7 (Hapten-A) to BSA (Immunogen-1)

To a solution of N-(5-carboxypentyl)-N-desethylmethoxetamine 7_(Hapten-A) (26.0 mg) in DMF (1.0 ml) was added N-(3-dimethylaminopropyl)-N'-ethylcarbodiimide hydrochloride EDC.HCl (73.7 mg) and N-hydroxysuccinimide (44.3 mg) and the mixture was incubated on the roller at room temperature overnight. This solution was added dropwise to a solution of BSA (100 mg, 1.5 μmol) in phosphate buffer saline (50 mM) (pH 8.0) (10 ml). The resulting solution was incubated on the roller at room temperature overnight. Excess hapten was removed by dialysis against phosphate buffer saline, pH 7.2 (3 changes) for 24 hours at 4° C., and freeze-dried. MALDI results showed 30.6 molecule of N-(5-carboxypentyl)-N-desethylmethoxetamine BSA__ (Immunogen-1) had been conjugated to one molecule of BSA. BSA attaches directly to the 5-carboxy group.

Example 9: Conjugation of N-(5-carboxypentyl)-N-desethylmethoxetamine 7 (Hapten-A) to KLH (Immunogen-2)

To a solution of N-(5-carboxypentyl)-N-desethylmethoxetamine 7 (Hapten-A)_(27.7 mg) in DMF (1.0 ml) was added N-(3-dimethylaminopropyl)-N'-ethylcarbodiimide hydrochloride EDC.HCl (73.7 mg) and N-hydroxysuccinimide (44.3 mg) and the mixture was incubated on the roller at room temperature overnight. This solution was added dropwise to a solution of KLH (100 mg) in phosphate buffer saline (50 mM) (pH 8.0) (10 ml). The resulting solution was incubated on the roller at room temperature overnight. Excess hapten was removed by dialysis against phosphate buffer saline, pH 7.2 (3 changes) for 24 hours at 4° C., and freeze-dried. KLH attaches directly to the 5-carboxy group.

Example 10: Conjugation of N-(5-carboxypentyl)-N-desethylmethoxetamine 7 (Hapten-A) to HRP (Tracer 1)

EDC hydrochloride (1.5 mg) was dissolved in water (0.5 ml) and immediately added to a solution of N-(5-carboxypentyl)-N-desethylmethoxetamine 7 (Hapten-A)_(3 mg) in DMF (0.2 ml). After mixing, this solution was added dropwise to a solution of HRP (20 mg) in water (1 ml). N-hydroxysuccinimide (1 mg) was added and the reaction mixture was incubated in the dark at room temperature overnight. Excess hapten was removed with double PD-10 columns (Pharmacia) in series, pre-equilibrated with PBS at pH 7.2. The hapten-HRP conjugate (tracer 1) was then dialysed overnignt against 10 L of PBS at pH 7.2 at 4° C. HRP attaches directly to the 5-carboxy group.

Example 11: Competitive Assay for Cross-Reactivity Measurement

A 96 well ELISA plate was coated with 125 µl/well of antibody (raised against Immunogen 2 (Example 9)) at an appropriate concentration prepared in Tris buffer and was incubated at 4° C. for overnight. Contents were tipped out and plate washed (×4) using TBST before 50 µl of appropriate cross-reactant was added at various concentrations from 0-10 ng/ml. 75 µl of tracer (Example 10—Tracer 1) was added to each well at an appropriate dilution, followed by incubation at 25° C. for 1 hour. Contents were tipped out and plate washed (×6) using TBST and 125 µl/well TMB solution was added. After 20 mins in dark, 125 µl/well 0.2M sulphuric acid was added. The plate was read at 450 nm using KC junior software.

Results

Data derived from FIGS. 5 to 7 is summarised in Table 1, using antibodies raised against Immunogen 2 (Example 9) and using Tracer 1 (Example 10)

Ave OD=average optical density
CV=coefficient of variation of OD
B=absorbance at 450 nm at x ng/ml standard concentration
$B_0$=absorbance at 450 nm at 0 ng/ml standard concentration
$IC_{50}$=standard concentration which produces 50% inhibition of maximal signal
$B/B_0=(B/B_0)\times100$
CR=cross-reactivity
CCR=competitive cross reactivity

TABLE 1

Antibody binding characteristics ($IC_{50}$ of antibody to methoxetamine <1.00 ng/ml raised against Immunogen 2 (Example 9) and using Tracer 1 (Example 10))

| Analyte | CCR |
|---|---|
| Methoxetamine | 100.00% |
| N-desethylmethoxetamine | >5.00% |
| Ketamine | <5.00% |
| Norketamine | <5.00% |
| Phencyclidine | <5.00% |
| Tramadol | <5.00% |
| Tilidine | <5.00% |

The maximum OD is the signal generated using tracer alone and 50% displacement (inhibition) corresponds to the $IC_{50}$ for that analyte. Relative competitive cross-reactivities of analytes were computed using $IC_{50}$ values. That is, the % CCR of the analyte is derived as follows (the analyte showing the greatest binding, methoxetamine, is given a % CCR of 100):

$IC_{50}$ analyte 1 (methoxetamine) divided by $IC_{50}$ analyte 2 (n-desmethylmethoxetamine, ketamine etc) multiplied by 100.

Thus the % CCR of N-desmethylmethoxetamine (compared to methoxetamine) (FIG. 5) is:

$0.47/1.96\times100=24\%$

As the other analytes show minimal binding, their curves do not fully form (flatten out) and a $B/B_0$ of 50 is not attained, hence the % CCR is represented as less than that corresponding to the highest concentration tested i.e. 10 ng/ml

$0.47/10\times100=<4.7\%$

This can also be represented as <<4.7% to show that the competitive cross-reactivities are considerably less than 4.7%.

Table 1 and FIGS. 5 to 7 show that the antibody of the invention has a high affinity for methoxetamine, exhibits substantial binding to the metabolite N-desethylmethoxetamine but does not bind to structurally similar drugs ketamine, tramadol and phencyclidine.

STATEMENTS OF THE INVENTION

1. An antibody which binds to an epitope of a molecule comprising the sub-structure

2. The antibody of statement 1 in which the sub-structure is

3. The antibody of statement 2 which has <5.00% cross-reactivity to ketamine, norketamine, tramadol and tilidine compared to 100% cross-reactivity to methoxetamine.

4. The antibody of the preceding statements which has an $IC_{50}$ of <10 ng/ml for methoxetamine.

5. The antibody of the preceding statements which is derived from an immunogen wherein X is —NH— or —N(R)— in which R is substituted or unsubstituted alkyl, n is 0 or 1 and the accm is an antigenicity conferring carrier material.

6. An immunoassay method of detecting or determining methoxetamine in an in vitro sample or in a solution comprising contacting the sample or solution with a detecting agent and an antibody of any of statements 1 to 5, detecting the bound detecting agent and deducing the presence or amount of methoxetamine.

7. The immunoassay method of statement 6 in which the detecting agent is in which Y is a crosslinker which links the detectable label to the cyclohexyl ring.

8. A kit comprising an antibody of any of statements 1 to 6 and optionally a detecting agent.

9. The kit of claim 8 in which the detecting agent is the structure of statement 7.

10. A substrate which supports the antibodies of any of statements 1 to 5.

11. An immunogen of structure wherein X is —NH— or —N(R)— in which R is substituted or unsubstituted alkyl, n is 0 or 1 and the accm is an antigenicity conferring carrier material.

The invention claimed is:

1. A polyclonal antibody raised against an immunogen having the structure of:

wherein KLH is keyhole limpet hemocyanin, wherein the polyclonal antibody binds to methoxetamine and N-desethylmethoxetamine, wherein the polyclonal antibody has a cross-reactivity of 24% for N-desmethylmethoxetamine, when compared to 100% cross-reactivity for methoxetamine and shows a cross-reactivity of less than 5.0% for each of ketamine, norketamine, phencyclidine, tramadol and tilidine, when compared to 100% cross-reactivity for methoxetamine; and wherein said cross reactivity is measured by using N-(5-carboxypentyl)-N-desethylmethoxetamine-HRP as a detecting agent, wherein HRP is horseradish peroxidase.

2. The polyclonal antibody of claim 1 which has an $IC_{50}$ of <1.00 ng/ml for methoxetamine.

3. The polyclonal antibody of claim 1, which has been purified.

4. A method of detecting or determining methoxetamine in a sample comprising:
   i) contacting the sample with a detecting agent and the polyclonal antibody of claim 1; and
   ii) detecting or determining the amount of the detecting agent bound to the antibody.

5. The method of claim 4 in which the detecting agent is N-(5-carboxypentyl)-N-desethylmethoxetamine-HRP.

6. The method of claim 5, wherein the presence of the detecting agent is detected or determined by a colour change in response to reaction of HRP with a substrate.

7. The method of claim 6, wherein the colour change is detected or determined by reading the absorbance at 450 nm.

8. A kit comprising the polyclonal antibody of claim 1.

9. The kit of claim 8, further comprising a detecting agent, wherein the detecting agent N-(5-carboxypentyl)-N-desethylmethoxetamine-HRP.

* * * * *